United States Patent [19]

Antonevich

[11] Patent Number: 4,475,141
[45] Date of Patent: Oct. 2, 1984

[54] BODY ELECTRICAL GROUNDING TETHER

[75] Inventor: John N. Antonevich, Lansdale, Pa.

[73] Assignee: The Simco Company, Inc., Hatfield, Pa.

[21] Appl. No.: 573,101

[22] Filed: Jan. 23, 1984

[51] Int. Cl.³ .............................................. H05F 3/02
[52] U.S. Cl. ...................................... 361/220; 57/901; 361/212
[58] Field of Search ............... 361/220, 212, 223, 224; 57/901

[56] References Cited

U.S. PATENT DOCUMENTS

| 3,699,590 | 10/1972 | Webber et al. | 57/901 X |
| 4,373,175 | 2/1983 | Mykkanen | 361/212 X |
| 4,398,277 | 8/1983 | Christiansen et al. | 361/220 |

FOREIGN PATENT DOCUMENTS 973750  10/1964  United Kingdom ................ 174/47

Primary Examiner—Reinhard J. Eisenzopf
Attorney, Agent, or Firm—Stanley Bilker

[57] ABSTRACT

A conductive strap for tethering personnel to electrical ground comprises a stretchable band of an elastomeric non-conductive fabric for resiliently embracing a body member in a closed loop. At least one row of a continuous conductive thread is embroidered to the interior surface of the band by a line of stitching which includes a non-conductive thread component penetrating through the fabric from the outside and interlocking with the interior conductive thread component, preferably sewn in a zig-zag pattern. The conductive thread is coupled to a clasp for electrical connection to ground through a cable tether.

9 Claims, 4 Drawing Figures

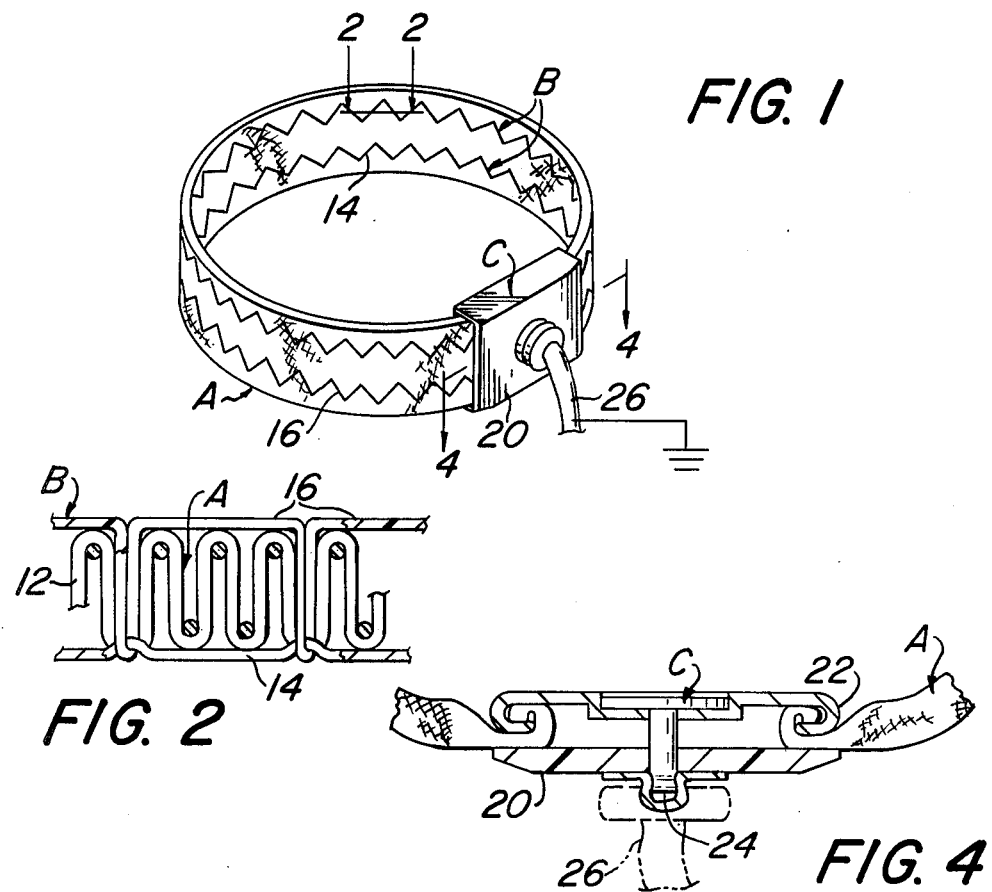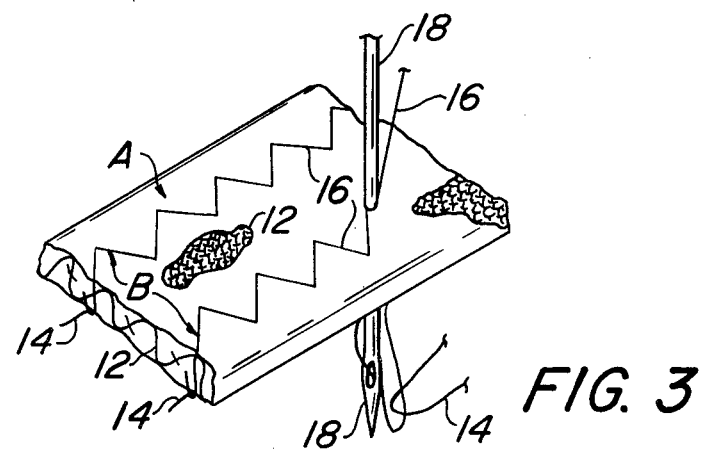

4,475,141

BODY ELECTRICAL GROUNDING TETHER

BACKGROUND OF THE INVENTION

A. Field of the Invention

This invention relates to electrically conductive grounding straps or tethers which are attached to the body by way of the individual's limbs in order to ground operating personnel and prevent build-up of static electricity on such persons. More particularly, this invention pertains to the strap means for attaching the ground tether to the body members and maintaining the electrically conductive portion of the strap in intimate electrical contact with the skin of the wearer. The invention is especially concerned with a non-conductive elastomeric fabric or knitted band to the interior surface of which is embroidered a continuous conductive thread, preferably sewn in a zig-zag or rick-rack pattern, so that the body member may be resiliently embraced in a closed self-adjusting loop.

B. Prior Art

In U.S. Pat. No. 4,398,277, there is shown an elastomeric body strap having a fabric band formed by at least one interlaced yarn which includes an end having an electrically conductive fiber plaited with an end having an elastomeric non-conductive fiber. The conductive yarn and the insulative yarn are plaited or knitted together to form interlocking loops which define two levels, an exterior insulated back with a conductive interior face. The foregoing patent and the references cited therein of record are generally representative of the prior state of the art.

C. Purpose

One of the inherent problems in making a knitted or plaited fabric from yarns of widely different elongation characteristics is in producing a generally uniform interwoven configuration wherein the loops are of consistent size, especially when elastomeric yarns are interlaced with brittle yarns employing metallic filaments. Not only is it desirable that even pressure be exerted upon the conductive yarns in contact with the wearer's skin so that electrical charges may be carried away from operating personnel, but also it is necessary that there be electrical continuity through the conductive yarn to ground. Breaking of the metallic elements as a result of failure of the conductive strands, for example, at the interlacing of the loops, can make the body tether completely inoperative as a consequence of electrical discontinuity.

It is therefore an object of this invention to provide an elastomeric body band for tethering operating personnel to electrical ground.

Another object of this invention is to provide a conductive stretchable body band in which the elastomeric portion urges the conductive portion against the skin of the wearer with uniform pressure.

Yet another object of this invention is to construct a stretchable conductive body band in which the means for attaching the conductive elements to the elastomeric elements provides maximum assurance against conductive strand breakage.

Yet still another object of this invention is to provide an elastomeric insulative body band in which a conductive thread is embroidered upon the surface of the band by a line of stitching wherein an insulative thread component having substantially the same elongation characteristics as the conductive thread component is interlocked with the latter at the interior face of the band.

Other objects of this invention are to provide an improved device of the character described which is easily and economically produced, sturdy in construction and both highly efficient and effective in operation.

SUMMARY OF THE INVENTION

In accordance with this invention, there is provided a grounding strap for tethering operating personnel to electrical ground wherein a stretchable fabric band is employed for elastically embracing one of the wearer's limbs in a closed self-adjusting loop. The band comprises an elastomeric fabric, preferably knitted or woven of a highly elongatable elastic yarn. A conductive thread is sewn or embroidered upon the inside surface of the band by a line of stitching in which a non-conductive thread component having substantially the same elongation characteristics penetrates the elastomeric fabric from the outside and interlocks with the interior conductive thread component. The stitching is preferably sewn in a zig-zag or rick-rack pattern so that the elastomeric band exerts uniform pressure upon the conductive thread against the skin of the wearer. Since the outside of the band, including the exterior non-conductive thread component, is entirely insulative in character, there is no danger of an external high voltage source contacting the conductive portion of the band from outside. The band may be formed by closing the free ends of an elastomeric strip by means of a mechanical coupling which also links the conductive element by way of an electrical cable to ground. The band may also be formed in the manner of a continuous seamless torus on conventional circular knitting machines.

BRIEF DESCRIPTION OF THE FIGURES

With the above and related objects in view, this invention consists of the details of construction and combination of parts as will be more fully understood from the following detailed description when read in conjunction with the accompanying drawing in which:

FIG. 1 is a perspective view of a body grounding strap embodying this invention.

FIG. 2 is a sectional view taken along lines 2—2 of FIG. 1.

FIG. 3 is a fragmentary perspective view showing the manner in which a conductive thread is embroidered in one or more lines of stitching by means of a sewing needle.

FIG. 4 is a sectional view taken along lines 4—4 of FIG. 1.

DETAILED DESCRIPTION OF PREFERRED EMBODIMENTS

Referring now in greater detail to the drawing in which similar reference characters refer to similar parts, there is shown a body strap for tethering personnel to electrical ground. The strap comprises a stretchable band A fabricated of an elastomeric, non-conductive fabric, conductive thread elements B sewn to the fabric in one or more lines of embroidered stitching, and a mechanical coupling C for electrically connecting the conductive element to electrical ground.

The stretchable band A is preferably knitted or woven from a non-conductive, highly-elongatable, elastic fiber 12, such as Spandex or Lycra, made by E. I. duPont de Nemours, of Wilmington, Del. The specific nature, composition or gauge of the yarn 12 is generally immaterial so long as it is non-conductive and the band from which it is formed is highly elastic and adapted to resiliently embrace the body limb, such as the wearer's wrist, in a closed loop. The band A may be constructed of a "seamless" closed torus, such as that made on circular knitting machines, or may be fabricated into a strip which is cut into appropriate lengths whose free ends are joined together into a closed loop by the mechanical coupling C, as shown in FIG. 4.

The conductive stitching element B is sewn to the band A as an embroidered line of stitching comprised of a conductive thread component 14 which lies on the interior surface of the band and a non-conductive or insulative thread component 16 which lies on the outside surface of the band, penetrates therethrough and interlocks with the conductive thread component 14. The stitching B may be applied in one or more lines by a conventional sewing machine employing a needle 18 which carries the upper thread 16 through the fabric interstices and into interlacing engagement with the lower or bobbin thread component 14, all in a conventional manner well known in the sewing art. Although not mandatory, it is preferable that the conductive thread component 14 and the insulative thread component 16 be comprised of elements having equivalent elongation characteristics to minimize undue stress on the more brittle conductive thread. It is also desirable that the insulative thread component 16 be the one which penetrates the fabric for the same reason. Appropriate adjustment of the spool and bobbin thread tension determines the degree of conductive thread penetration.

The electrically conductive thread 14 may be constituted of a plurality of metallic fibers, such as stainless steel, intertwined with a non-conductive strand, such as polyester filaments to define a twisted composite, for example, Bekitex BK conductive yarn, licensed under U.S. Pat. No. 3,987,613. The insulative thread 16 may be any conventional non-conductive composition, including but not limited to cotton, rayon, nylon or polyester. It is preferable that the lines of stitching B be configured in a zig-zag or rick-rack pattern to accommodate the expansion and contraction of the embroidery with the elasticity of the elastomeric band A.

The mechanical coupling C for electrically connecting the conductive thread 14 to ground (and joining the free ends of the band strip where required) comprises, for example, a channel-shaped insulative clamp portion 20 into which is pressed a metallic plate 22. The plate 22 may have a plurality of serrations or teeth which run transversely to the direction of the stitch lines A and bite into good electrical contact with the interior conductive thread 14. A conductive snap fastener 24 projects from the metal plate 22 through the clamp portion 20 and to the end of which is resiliently engaged the complementary terminal of an electrical cable 26 for carrying charges to ground.

As is apparent from the foregoing description, the elastomeric band A resiliently embraces the limb of the wearer in a wide range of elastic self-adjustment and uniformly presses the conductive stitching 14 at the interior band face against the skin. Embroidering the stitching rather than knitting the same minimizes breakage of the normally fragile conductive thread 14.

Although this invention has been described in considerable detail, such description is intended as being illustrative rather than limiting, since the invention may be variously embodied without departing from the spirit thereof, and the scope of the invention is to be determined as claimed.

What is claimed is:

1. A conductive body strap for tethering personnel to electrical ground comprising:
    a stretchable band adapted to elastically embrace a body member in a closed loop, said band having inner and outside surfaces and including an elastomeric fabric formed of a nonconductive yarn.
    embroidered stitching sewn to said fabric along said band, said embroidered stitching including a substantially continuous conductive thread component lying upon the inner surface of said band, and
    coupling means for electrically connecting said conductive thread component through an electrical cable to ground.

2. The conductive strap of claim 1 wherein said embroidered stitching includes at least one row of zig-zag elements arranged in a rick-rack pattern.

3. The conductive strap of claim 1 wherein said band comprises an elastomeric fabric knitted from insulative elastomeric yarn as a strip having free ends, and mechanical means connecting the free ends of said strip into the closed loop.

4. The conductive strip of claim 3 wherein said mechanical means includes said coupling means.

5. The conductive strip of claim 1 wherein said embroidered stitching includes an insulative thread component attached the outside surface of said band and penetrating through said elastomeric fabric into interlocking engagement with said conductive thread component.

6. The conductive strap of claim 5 wherein said conductive thread component comprises a conductive filament intertwined with a non-conductive fiber.

7. The conductive strap of claim 5 wherein said embroidered stitching is arranged in at least one zig-zag line of rick-rack elements.

8. The conductive strap of claim 1 wherein said coupling means comprises a clamp.

9. The conductive strap of claim 8 wherein said clamp includes an exterior insulative portion and a conductive interior portion.

* * * * *